(12) United States Patent
Seo et al.

(10) Patent No.: US 11,441,258 B2
(45) Date of Patent: Sep. 13, 2022

(54) CLOTHING TREATMENT APPARATUS AND CONTROLLING METHOD THEREOF

(71) Applicant: Samsung Electronics Co., Ltd., Suwon-si (KR)

(72) Inventors: Dongpil Seo, Suwon-si (KR); Kisun Park, Suwon-si (KR); Jaeryong Park, Suwon-si (KR); Jungsang Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 591 days.

(21) Appl. No.: 16/563,115

(22) Filed: Sep. 6, 2019

(65) Prior Publication Data
US 2020/0080253 A1 Mar. 12, 2020

(30) Foreign Application Priority Data
Sep. 12, 2018 (KR) .......................... 10-2018-0109261

(51) Int. Cl.
*D06F 73/02* (2006.01)
*A61L 2/07* (2006.01)
*A61L 2/26* (2006.01)

(52) U.S. Cl.
CPC ................ *D06F 73/02* (2013.01); *A61L 2/07* (2013.01); *A61L 2/26* (2013.01); *A61L 2202/14* (2013.01); *A61L 2202/26* (2013.01)

(58) Field of Classification Search
CPC .......... A61L 2/07; A61L 2/26; A61L 2202/14; A61L 2202/26; D06F 73/02
See application file for complete search history.

(56) References Cited

U.S. PATENT DOCUMENTS

| | | | |
|---|---|---|---|
| 9,107,973 B1* | 8/2015 | Robinson | .................. A61L 2/10 |
| 9,506,185 B2 | 11/2016 | Choi et al. | |
| 9,873,971 B2 | 1/2018 | Park et al. | |
| 2011/0005279 A1 | 1/2011 | Yoo et al. | |

(Continued)

FOREIGN PATENT DOCUMENTS

| | | |
|---|---|---|
| JP | 2013-94325 A | 5/2013 |
| JP | 2014-42701 | 3/2014 |

(Continued)

OTHER PUBLICATIONS

International Search Report and Written Opinion of the International Searching Authority dated Dec. 17, 2019 in International Patent Application No. PCT/KR2019/011334.

*Primary Examiner* — Sean E Conley
(74) *Attorney, Agent, or Firm* — Staas & Halsey LLP (57) ABSTRACT

A clothing treatment apparatus is provided. The clothing treatment apparatus according to an embodiment includes a body including a storage chamber that stores clothing, a spray member configured to spray steam toward the clothing, a steam generator configured to supply steam to the spray member, a cabinet provided under the storage chamber, and a water supply container configured to store water inside, the water supply container being detachably combined with the cabinet, wherein the cabinet includes a cabinet plate formed with a supply hole that connects the water supply container to the steam generator and a discharge hole that drains residual water discharged when the water supply container is detached.

9 Claims, 9 Drawing Sheets

(56) References Cited

U.S. PATENT DOCUMENTS

| | | |
|---|---|---|
| 2014/0238086 A1 | 8/2014 | Choi et al. |
| 2016/0177490 A1 | 6/2016 | Park et al. |
| 2021/0301457 A1* | 9/2021 | Choi ................. D06F 58/12 |

FOREIGN PATENT DOCUMENTS

| | | |
|---|---|---|
| KR | 10-0479084 B1 | 3/2005 |
| KR | 10-0846471 B1 | 7/2008 |
| KR | 10-2009-0105126 | 10/2009 |
| KR | 10-0928686 B1 | 11/2009 |
| KR | 10-2011-0009919 A1 | 1/2011 |
| KR | 10-2013-0106193 | 9/2013 |
| KR | 10-2014-0108454 | 9/2014 |
| KR | 10-1597104 | 2/2016 |

* cited by examiner

CLOTHING TREATMENT APPARATUS AND CONTROLLING METHOD THEREOF

CROSS-REFERENCE TO RELATED APPLICATIONS

This application is based on and claims priority under 35 U.S.C. § 119 to Korean Patent Application No. 10-2018-0109261, filed on Sep. 12, 2018, in the Korean Intellectual Property Office, the disclosure of which is incorporated herein by reference in its entirety.

BACKGROUND

1. Field of the Invention

Devices and methods consistent with what is disclosed herein relate to a clothing treatment apparatus for improving the condition of clothing and a controlling method thereof.

2. Description of the Related Art

In general, a washing machine is widely used as a device for cleaning products made of fabrics such as clothing, bedding, etc. The functions of dehydration and drying are added to the washing machine since laundry is washed through friction between water contained in a container and the laundry.

Recently, as an apparatus capable of managing clothing more easily than a conventional washing machine, clothing treatment apparatuses including the functions of removing wrinkles, dust or smell of clothing without an additional washing process through cleaning water have been used.

The clothing treatment apparatus may remove odors, wrinkles, or moisture remaining in clothing by spraying hot steam on the clothing. The clothing treatment apparatus needs be equipped with a water supply container to supply water to a steam generator that generates steam, and a drain container needs to be provided to drain condensed water generated by the clothing treatment apparatus to the outside.

SUMMARY

An aspect of the embodiments relates to providing a clothing treatment apparatus capable of preventing water leakage that may occur in a process of detaching a water supply container that supplies water to the clothing treatment apparatus and a controlling method thereof.

According to an embodiment, there is provided a clothing treatment apparatus for preventing overflowing water of a water collecting space that temporarily stores condensed water and residual water and a controlling method thereof.

According to an embodiment, there is provided a clothing treatment apparatus including a body including a storage chamber that stores clothing, a spray member configured to spray steam toward the clothing, a steam generator configured to supply steam to the spray member, a cabinet provided under the storage chamber, and a water supply container configured to store water inside, the water supply container being detachably combined with the cabinet, wherein the cabinet includes a cabinet plate formed with a supply hole that connects the water supply container to the steam generator and a discharge hole that drains residual water discharged when the water supply container is detached.

The cabinet plate may include an inclined surface that is formed to be inclined downwardly toward the discharge hole.

The apparatus may further include a duct formed with a water collecting space for collecting condensed water generated from inside the clothing treatment apparatus, wherein the discharge hole is connected to the duct.

The apparatus may further include a discharge route including one side connected to the discharge hole, and the other end connected to an inlet hole formed in the duct.

The discharge hole may be formed above the inlet hole formed in the duct.

The duct may include a sensor provided in the water collecting space for detecting a level of water in the water collecting space.

The apparatus may further include a drain pump configured to pump condensed water collected in the water collecting space, and a drain container configured to store water supplied by the drain pump.

The apparatus may further include a processor configured to confirm an amount of water in the water collecting space based on the level of water detected by the sensor, and based on the amount of water in the water collecting space being equal to and more than a predetermined amount, control the drain pump to supply the water in the water collecting space to the drain container.

The processor may be further configured to control the drain pump to supply the water in the water collecting space to the drain container at a predetermined period of time.

According to an embodiment, there is provided a controlling method of a clothing treatment apparatus, the method including detecting a level of water in a duct in which condensed water generated from inside the clothing treatment apparatus is collected, determining whether the detected level of water of the duct is a full level, supplying the water stored in the duct to a drain container based on the level of water in the duct being the full level, and supplying the water stored in the duct to the drain container on a regular basis in line with the detecting of the level of water in the duct.

The clothing treatment apparatus according to an embodiment of the disclosure having the structure described above may prevent water leakage that may occur in the process of installing a water supply tank, and prevent of a problem of overflowing water in the water collecting space.

DETAILED DESCRIPTION OF EXEMPLARY EMBODIMENTS

Hereinafter, embodiments of the clothing treatment apparatus according to the disclosure will be described in detail with reference to the accompanying drawings.

The disclosure is not limited to an embodiment disclosed below and may be implemented in various forms and the scope of the disclosure is not limited to the following embodiments. In addition, all changes or modifications derived from the meaning and scope of the claims and their equivalents should be construed as being included within the scope of the disclosure. In the following description, the configuration which is publicly known but irrelevant to the gist of the disclosure could be omitted. In addition, the attached drawings are not drawn to scale to facilitate understanding of the disclosure, but the dimensions of some of the components may be exaggerated.

The terms such as "first," "second," and so on may be used to describe a variety of elements, but the elements should not be limited by these terms. The terms are used simply to distinguish one element from other elements. The use of such ordinal numbers should not be construed as limiting the meaning of the term. For example, without departing from the scope of the disclosure, the first component may be referred to as a second component, and similarly, the second component may also be referred to as a first component.

Unless otherwise defined, all terms (including technical and scientific terms) used herein have the same meaning as commonly understood by one of ordinary skill in the art to which this disclosure belongs.

In addition, the terms such as 'front end', 'rear end', 'top portion', 'bottom portion', 'top end' and 'bottom end' used in the disclosure are defined on the basis of the drawings. However, the shape and the position of each constituent element are not limited to those terms.

Figure 1:
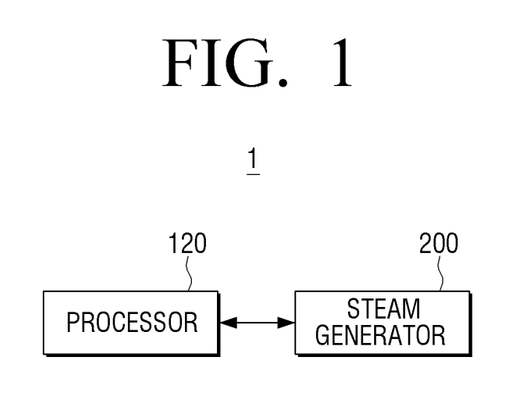
FIG. 1 is a block diagram to explain a simple configuration of a clothing treatment apparatus according to an embodiment of the disclosure.

FIG. 1 is a block diagram to explain a simple configuration of a clothing treatment apparatus according to an embodiment of the disclosure.

Referring to FIG. 1, a clothing treatment apparatus 1 may include a steam generator 200 and a processor 120.

The clothing treatment apparatus 1 may perform a plurality of functions. For example, the clothing treatment apparatus 1 may perform a plurality of functions such as heating, steaming, drying, dust removal, etc.

Figure 2:
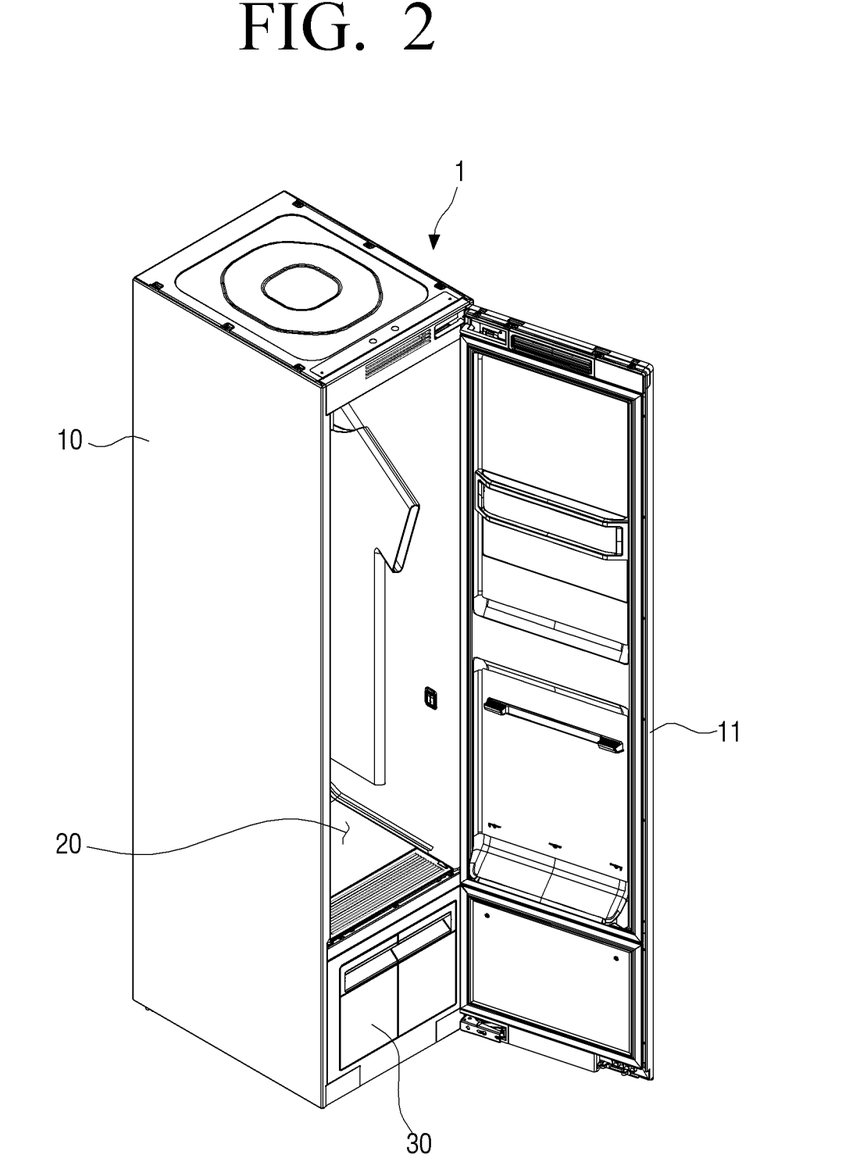
FIG. 2 is a perspective view illustrating a clothing treatment apparatus according to an embodiment of the disclosure.

The steam generator 200 may generate steam by receiving water from a water supply container 110 (please see FIG. 2). The detailed structure of the steam generator 200 will be described below.

The processor 120 may perform controlling of each constituent element in the clothing treatment apparatus 1. For example, the processor 120 may control the operation of the steam generator 200 when there is a need for performing a steam function.

The processor 120 may control each constituent element of the clothing treatment apparatus 1 to perform functions of heating, steaming and drying from among a plurality of functions.

The processor 120 may confirm the level of water stored in the duct 211 (see FIG. 4) of the steam generator 200, and control a drain pump 225 to supply water of the duct 211 to a drain container 130 (see FIG. 3) when the amount of water inside the duct 211 is equal to or more than a predetermined amount.

The processor 120 may control the drain pump 225 to supply water inside the duct 211 to the drain container 130 at predetermined intervals on a regular basis.

The detailed operation of controlling the drain pump 225 by the processor 120 will be described below.

FIG. 2 is a perspective view illustrating a clothing treatment apparatus according to an embodiment of the disclosure.

Referring to FIG. 2, a clothing treatment apparatus 1 may include a body 10 in which a storage chamber 20 and an electric chamber 30 are formed and a door 11 for opening and closing the storage chamber 20.

The storage chamber 20 may store clothes, and the electric chamber 30 may be equipped with various components for removing wrinkles, odors, or moisture that remain in the clothes through dehumidifying, heating or circulating function by circulating air of the storage chamber 20.

The storage chamber 20 may be equipped with a steam spray member (not shown). The steam spray member (not shown) may be mounted at a predetermined position of the storage chamber 20 so that steam generated by the steam generator 200 (see FIG. 3) may be sprayed to the stored clothing.

The electric chamber 30 may be provided in the lower portion of the body 10, that is, under the storage chamber 20. The storage chamber 20 and the electric chamber 30 may be divided by a partition wall.

Hereinafter, the configurations inside the electric chamber 30 of the clothing treatment apparatus according to an embodiment of the disclosure will be described in detail.

Figure 3:
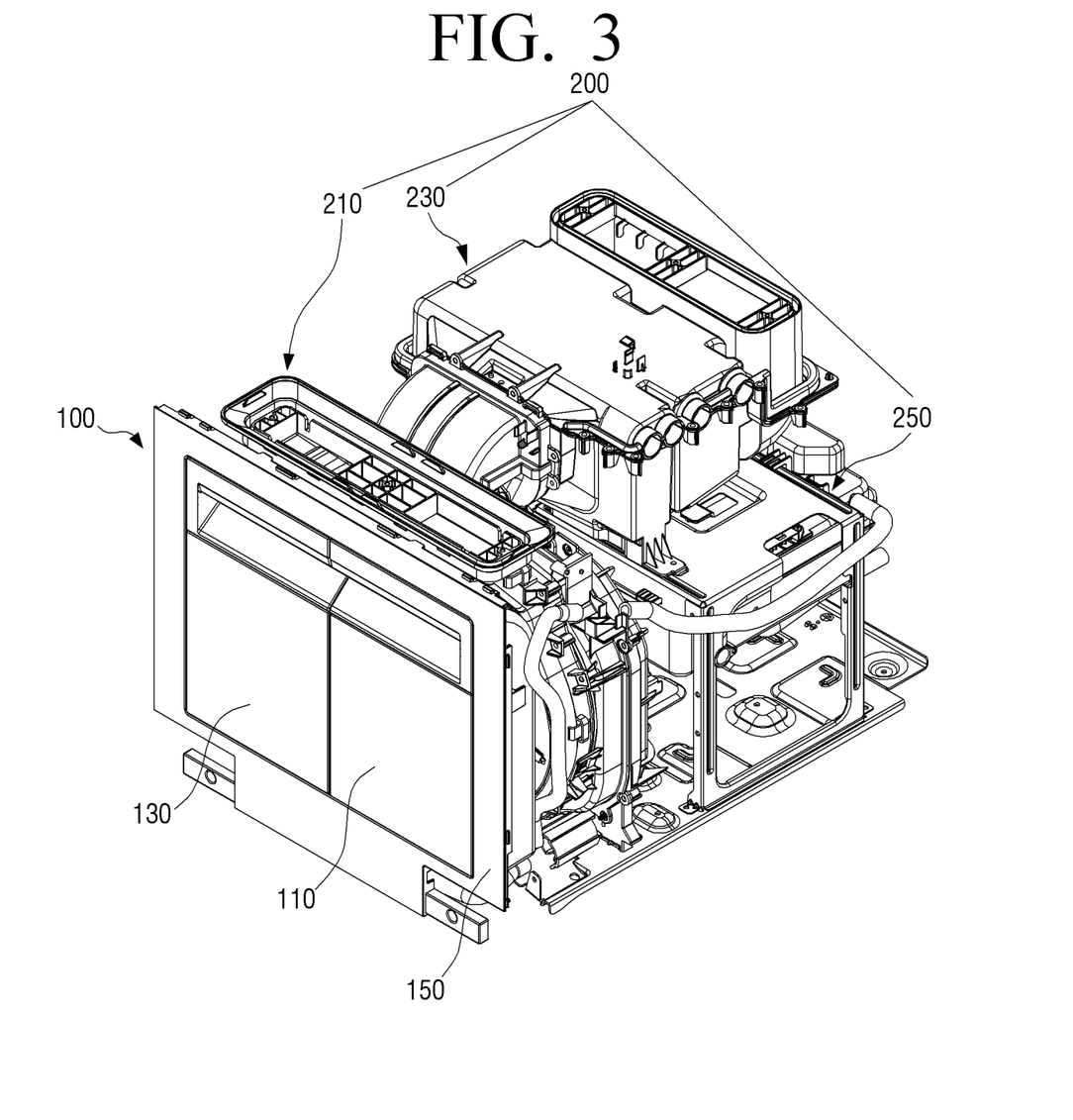
FIG. 3 is a perspective view illustrating the inside an electric chamber of a clothing treatment apparatus according to an embodiment of the disclosure.
Figure 4:
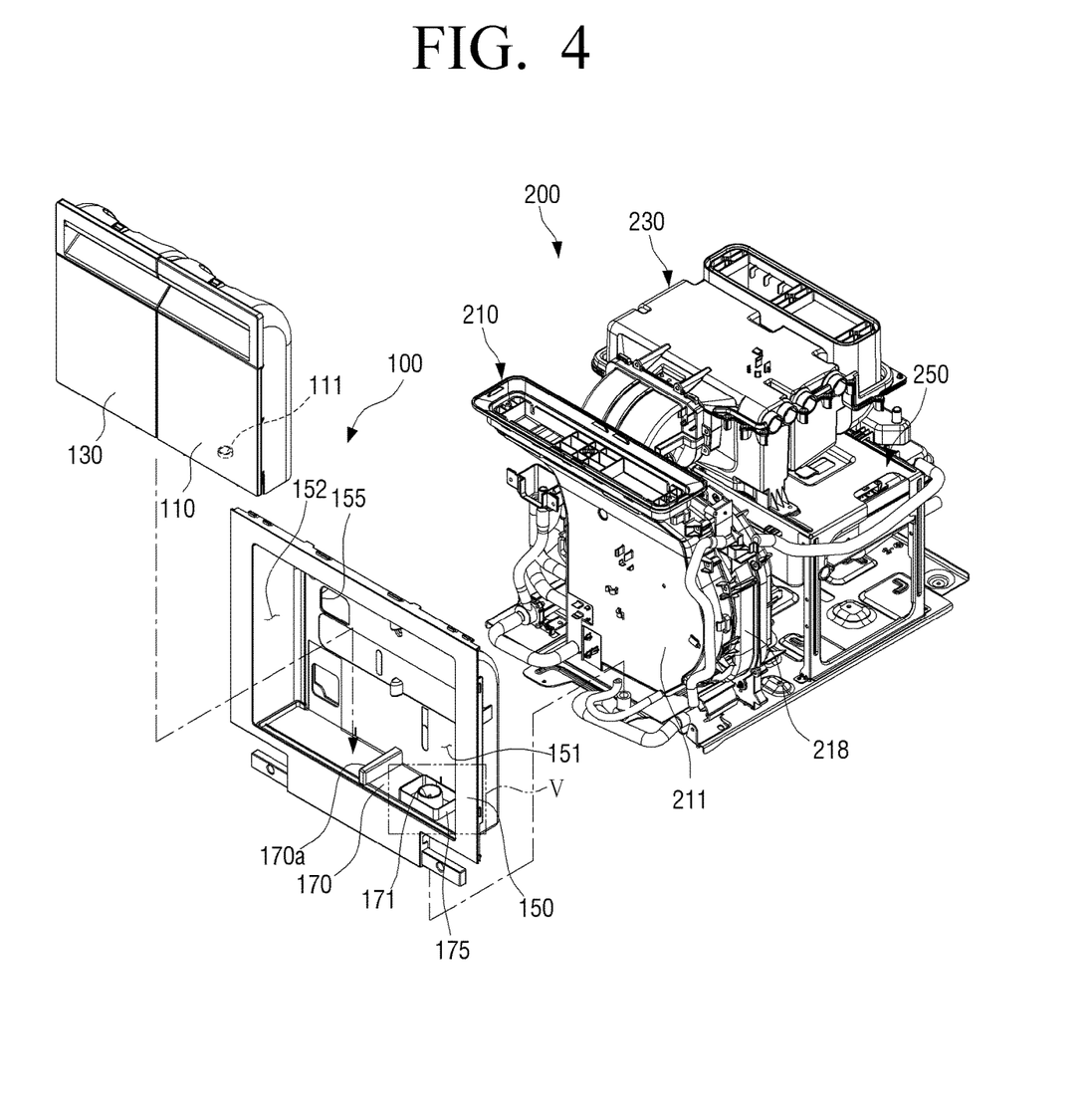
FIG. 4 is an exploded perspective view inside the electric chamber shown in FIG. 3.

FIG. 3 is a perspective view illustrating the inside an electric chamber of a clothing treatment apparatus according to an embodiment of the disclosure, and FIG. 4 is an exploded perspective view inside the electric chamber shown in FIG. 3.

Referring to FIG. 3 and FIG. 4, the electric chamber 30 may include a steam generator 200 that generates steam supplied to the storage chamber 20 for storing clothes, and a water container 100 provided in front of the electric chamber 30 for storing water.

The steam generator 200 may include a blowing device 210 for circulating air in the storage chamber 20, a heat pump 230 for air conditioning the air of the storage chamber 20, and a steam device 200 for supplying steam to the storage chamber 20.

The steam generator 200 may further include the processor 120 for controlling the blowing device 210, the steam device 250 and the heat pump 230. The processor 120 may control each constituent element of the clothing treatment device 1 based on information input by a user.

It has been described that the processor 120 is included in the steam generator 200, but is not limited thereto. The processor 120 may be included in the clothing treatment apparatus 1.

The steam generator 200 may be defined by an assembly of machine devices for driving each operation of the clothing treatment device 1 such as the blowing device 210, the steam device 250 and the heat pump 230.

The blowing device 210 may include a blowing fan 218 that inhales air from the storage chamber 20 by circulating air and discharges the air to the heat pump 230, and a duct 211 mounted on the inhalation side of the blowing fan 218 and allowing air inside the storage chamber 20 to flow into the blowing fan 28.

A water collecting space 212 (see FIG. 8) for collecting condensed water generated by the storage chamber 20 may be provided under the duct 211. The structure of the water collecting space 212 of the duct 211 will be described below.

The steam device 250 may be heated by an applied power source, and supplied with water from the water supply container 110 to change the water into steam. The steam may be supplied to the storage chamber 20, and moved to the storage chamber 20 by the heat pump 230.

The heat pump 230 may include a cooling cycle including a compressor, a condenser, an evaporator, and expansion valve, and may provide cooled air and heated air into the inside of the storage chamber 20 according to an operation mode.

The water container 100 may include a water supply container 110 for storing water for providing water to the steam generator 200 and a drain container 130 for storing the condensed water generated from inside of the clothing treatment apparatus 1 to the outside. The water container 100 may include a cabinet 150 for supporting the water supply container 110 and the drain container 130.

The water container 100 may be provided in front of the steam generator 200. The cabinet 150 in which the water supply container 110 and the drain container 130 are detachably mounted may be provided in front of the duct 211.

The water supply container 110 may supply water in connection with the steam device 250, and the drain container 130 may store water flowing from the water collecting space 212 of the duct 211 in connection with the duct 211.

A water supply check valve 111 mounted on the cabinet 150 to open and close a flow path connected to the steam device 250 may be provided in the lower portion of the water supply container 110. The water supply check valve 111 may control water inside the water supply container 110 in combination with a check valve hole (not shown) formed in the lower portion of the water supply container 110.

The water supply check valve 111 may move water inside the water supply container 110 to the steam device 250 when the waster supply container 110 is mounted on the cabinet 150, but prevent the water in the steam device 250 from flowing into the water supply container 110.

The water supply check valve 111 may supply water in the water supply container 110 to the steam device 250 intermittently depending on whether the water supply container 110 is mounted on the cabinet 150.

The water supply check valve 111 may include one side protruding downwardly, and be pushed and moved upwardly when the water supply container 110 is combined with the cabinet 150. A supply path 251 (see FIG. 7) connected to the steam device 250 may be opened by the movement of the water check valve 111, and the water in the water supply container 110 may flow to the cabinet 150.

When the water supply container 110 is separated from the cabinet 150, the water supply check valve 111 may move downwardly by elasticity to close the water supply container 110.

It has been described that water inside the water supply container 110 is supplied to the steam device 250 intermittently through the water supply check valve 111, but the disclosure is not limited thereto. A feature for intermittently supplying water of the water supply container 110 to the steam device 250 may be included.

The drain container 130 may be functionally similar to the water supply container 110, and formed symmetrically in the vertical direction. However, the drain container 130 may be provided with a check valve (not shown) on a rear side instead of a lower side.

The drain container 130 may store water supplied from the duct 211 in which condensed water generated by the storage chamber 20 and condensed water generated by the heat pump 230 are stored.

The cabinet 150 may be configured to form a lower portion of the body 10, and it may be connected to the body 10 or integrally formed with the body 10.

The cabinet 150 may include a first mounting portion 151 on which the water supply container 110 is mounted, and a second mounting portion 153 on which the drain container 130 is mounted. A cabinet plate 170 may be provided under the cabinet 150. The cabinet plate 170 may support the lower portions of the water supply container 110 and the drain container 130.

The cabinet plate 170 may have a partition wall 170a for dividing the first mounting portion 151 and the second mounting portion 153 at its center.

The cabinet plate 170 may include a supply hole 171 in combination with the water supply check valve 111 of the water supply container 110 and a discharge hole 173 (see FIG. 5) for discharging residual water that could flow out of the water supply container 110. The supply hole 171 and the discharge hole 173 will be described below.

The cabinet plate 170 may further include a water frame 175 formed to surround the supply hole 171 and the discharge hole 173. The water frame 175 may be formed to have a shape corresponding to the lower portion of the water supply container 110, and the water frame 175 may not be formed on the cabinet plate 175 according to the lower portion structure.

A drain opening 155 connecting the drain container 130 to the water collecting space 212 of the duct 211 may be formed on the rear surface of the second mounting portion 153. A check valve (not shown) formed on the rear surface of the drain container 130 may be accommodated in the drain opening 155, and the check valve may be connected to the drainage 220 (see FIG. 5) that discharges condensed water pumped by the drain pump 225 (see FIG. 7).

Figure 5:
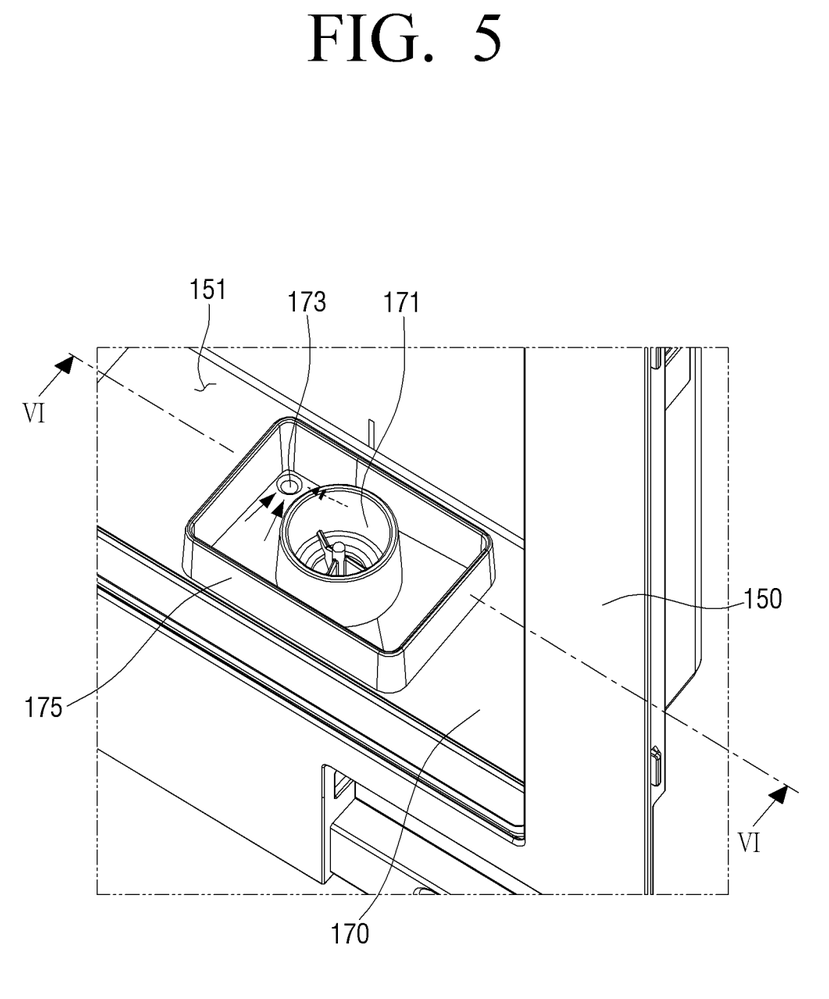
FIG. 5 is an enlarged view of '□' shown in FIG. 4.
Figure 6:
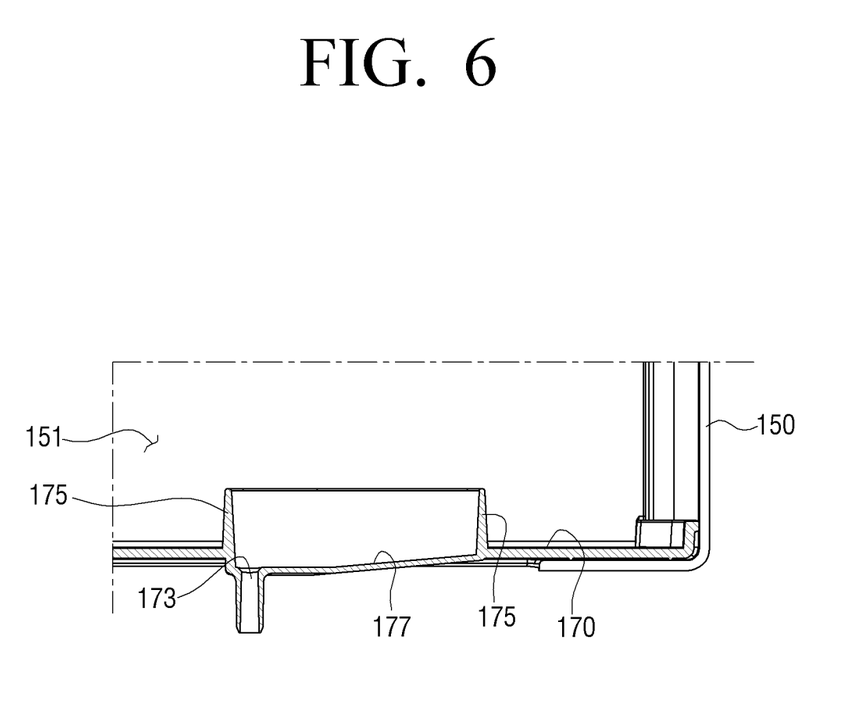
FIG. 6 is a cross-sectional view taken along line □-□ shown in FIG. 5.

FIG. 5 is an enlarged view of '□' shown in FIG. 4, and FIG. 6 is a cross-sectional view taken along line □-□ shown in FIG. 5.

Referring to FIG. 5, the discharge hole 173 may be formed on the cabinet plate 170, and the water frame 175 may be formed to surround the discharge hole 173.

The discharge hole 173 may be connected to the duct 211 for storing water temporarily. The water discharged through the discharge hole 173 may flow to the water collecting space 212 of the duct 211.

A small amount of water may be discharged from the water supply container 110 through the water supply check valve 111 of the water supply container 110 in the process of mounting and detaching the water supply container 110.

When the water supply container 110 is mounted on or detached from the cabinet 150, the water supply check valve 111 of the water supply container 110 may be opened for a short period of time, and water of the water supply container 110 may be discharged through the water supply check valve 111.

The residual water discharged from the water supply container 110 may be formed in the vicinity of the supply hole 171, and stored in the space surrounded by the water frame 175. The residual water stored inside the water frame 175 may be discharged to the discharge hole 173.

When the water frame 175 is not formed, the residual water may be stored in the space formed in the cabinet plate 170, and the residual water stored on the cabinet plate 170 may be discharged to the discharge hole 173 in the same manner.

The residual water stored in the cabinet plate 170 or the water frame 175 may be discharged to the discharge hole 173.

Referring to FIG. 6, the cabinet plate 170 may be formed to be inclined downwardly toward the discharge hole 173. The cabinet plate 170 may include an inclined surface 177 inclined downwardly toward the discharge hole 173. In other words, the discharge hole 173 may be formed at the lowermost of the cabinet plate 170.

Accordingly, the residual water stored in the cabinet plate 170 may flow toward the discharge hole 173 along the inclined surface 177.

In the same manner, the residual water stored inside the water frame 175 may flow toward the discharge hole 173 along the inclined surface 177 of the cabinet plate 170, and move to the water collecting space 212 of the duct 211 connected to the discharge hole 173.

When water overflows in the cabinet 150, water may overflow to the outside of the clothing treatment apparatus 1, and the overflowed water may cause a failure of the electrical heater, etc. embedded in the clothing treatment apparatus 1. Therefore, the residual water in the cabinet 150 needs to be recollected.

The clothing treatment apparatus 1 may discharge the residual water discharged through the discharge hole 173 to the duct 211, thereby preventing water from overflowing from the cabinet 150 through repeated detachment of the water supply container 110.

The residual water discharged from the water supply container 110 may be discharged through the drain container 130 via the duct 211. The flowing path of water will be described below.

Figure 7:
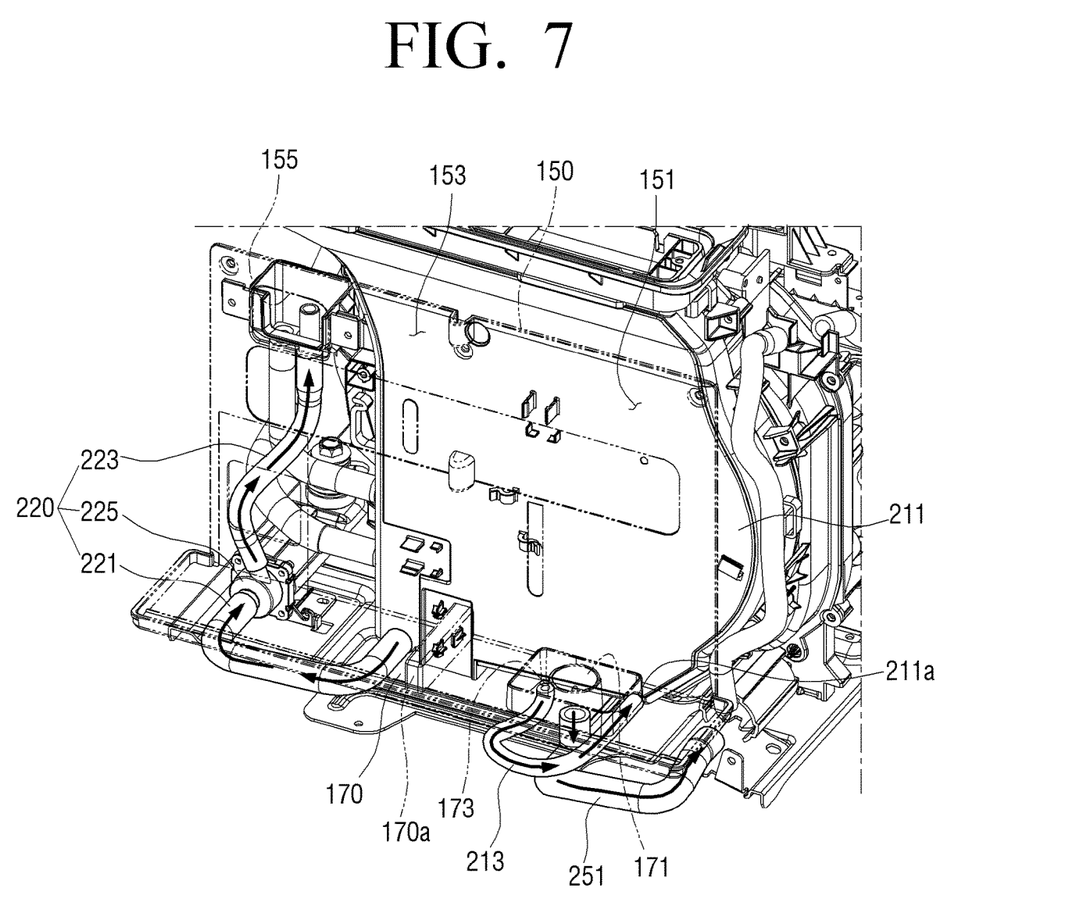
FIG. 7 is a perspective view illustrating a part of a cabinet and a part of a steam generator according to an embodiment of the disclosure.

FIG. 7 is a perspective view illustrating a part of a cabinet and a part of a steam generator according to an embodiment of the disclosure.

Referring to FIG. 7, a steam generator 200 may include a supply route 251 for connecting the water supply container 110 to the steam device 250, a discharge route 213 for connecting the discharge hole 173 to the duct 211, and a drainage 220 for connecting the duct 211 to the drain container 130.

The supply route 251 for connecting the water supply container 110 to the steam device 250 may have one end connected to the supply hole 171, and the other end connected to the steam device 250. The supply route 171 may be combined with the water supply check valve 111 of the water supply container 110 to supply water of the water supply container 110 to the steam device 250 through the supply route 251.

The drainage 213 may have one end connected to the discharge hole 173, and the other end connected to the duct 211. An inlet hole 211a connected to the other end of the drainage 213 may be formed in the lower portion of the duct 211. The residual water discharged from the discharge hole 173 may flow into the inlet hole 211a of the duct 211 along the drainage 213 to flow toward the water collecting space 212.

The discharge hole 173 may be formed above the inlet hole 211a. Accordingly, the residual water discharged through the discharge hole 173 may flow into the inlet hole 211a of the duct 211 by the height difference to flow toward the water collecting space 212.

The residual water discharged from the water supply container 110 may move to the duct 211 without an additional driving source.

The drainage 220 may have one end connected to the duct 211 and other end connected to the drain container 130.

The drainage 220 may include the draining pump 225. Water stored in the water collecting space 212 of the duct 211 may move toward the drain container 130 by pumping the drain pump 225.

The drainage 220 may consist of a first drainage 221 including one end connected to the duct 221 and the other end connected to the discharge pump 225, and a second drainage 223 including one end connected to the drain pump 225 and the other end connected to the drain container 130.

The water collecting space 212 of the duct 211 may be disposed above the drain container 130, so that the height difference between the draining container 130 and the water collecting space 212 of the duct 21 may be compensated by using the discharging pump 225.

The electric chamber 30 shown in FIG. 2 may be equipped with the drain container 130. The condensed water compressed by the heat pump 230 may be collected in the water collecting space 212 formed in the lower portion of the duct 211, and water collected in the water collecting space 212 may move to the drain container 130 to be stored.

Hereinafter, the water collecting space 212 of the duct will be described in detail.

Figure 8:
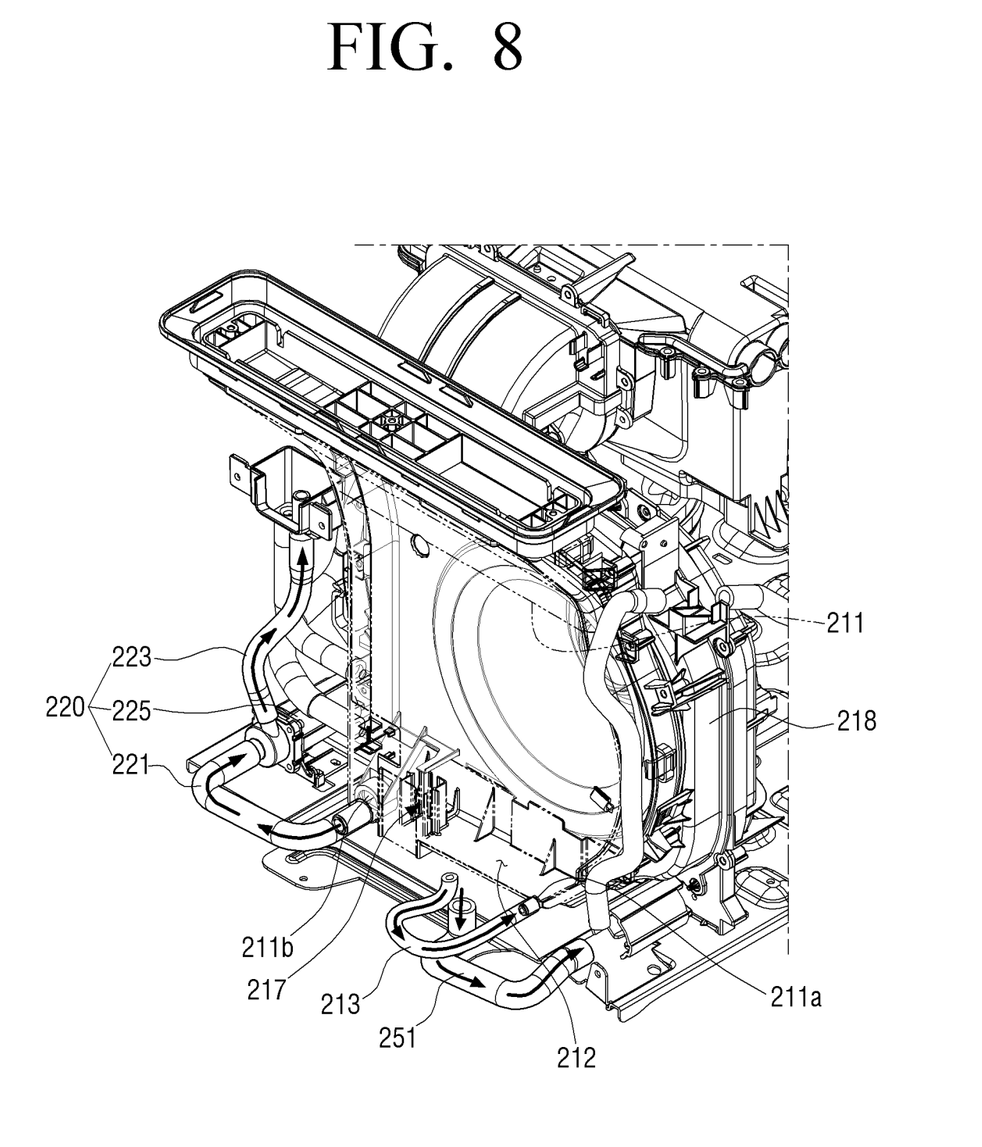
FIG. 8 is a perspective view illustrating a part of a steam generator according to an embodiment of the disclosure.

FIG. 8 is a perspective view illustrating a part of a steam generator according to an embodiment of the disclosure. FIG. 8 illustrates the duct 211 as being transparent to explain the water collecting space 212 formed inside the duct 211.

Referring to FIG. 8, the water collecting space 212 may be formed inside the duct 211. The water collecting space 212 may be formed in the lower portion of the duct 211, and formed as a space surrounded by a side wall to store water.

The inlet hole 211a through which the residual water flows from the discharge hole 173 may be formed on one side of the water collecting space 212. The inlet hole 211a may be connected to the discharge hole 173 via the discharge route 213. The inlet hole 211a may be formed under the discharge hole 173 to be supplied with the residual water from the discharge hole 173 due to the height difference. The residual water flowing through the drainage 213 may flow into the water collecting space 212 through the inlet hole 211a.

The residual water flowing into the water collecting space 212 through the discharge hole 173 may be transferred to the drain container 130 through the drain hole 211b. Therefore, the residual water that flow out while the cabinet 150 is coupled to the water supply container 110 may move to the drain container 130 to be discharged to the outside.

The drain hole 211b connected to the drain container 130 may be formed on the other side of the water collecting space 212. The water stored in the water collecting space 212 may be transferred to the drain container 130 through the drain hole 211b. The water stored in the water collecting space 212 may be discharged to the drain hole 211b using the drain pump 225, and transferred to the first drainage 221, the drain pump 225, and the second drainage 223 to be stored in the drain container 130.

The water collecting space 212 may temporarily store the residual water for discharging the residual water discharged in the process of detaching the water supply container 110 to the drain container 130 as well as collecting the condensed water generated by the storage chamber 20. The condensed water compressed by the storage chamber 20 may not be discharged to the drain container 130, but discharged to the drain container 130 via the water collecting space 212. When the condensed water is temporarily stored in the water collecting space 212 and discharged to the drain pump 225, it could be discharged with the residual water discharged in the process of detaching the water supply container 110. Therefore, it becomes more convenient to drain the water.

The water stored in the drain container 130 may selectively separate the drain container 130 from the electric chamber 30 by the user of the clothing treatment apparatus 1 to discharge the water stored inside the drain container 130 to the outside.

A sensor 217 for sensing the level of water of the water collecting space 212 may be provided.

The processor 120 may identify the amount of water of the water collecting space 212 based on the level of water sensed by the sensor 217, and if the amount of water in the water collecting space 212 is equal to or more than a predetermined amount, may control the drain pump 225 to supply water to the drain container 130.

If the amount of water in the water collecting space 212 sensed by the sensor 217 is equal to or more than a predetermined amount, the drain pump 225 may move the water stored in the water collecting space 212 to the water supply container 110 by pumping the water.

The processor 120 may control the drain pump 225 to supply water of the water collecting space 212 to the drain container 130 at a predetermined period of time separately from the level of water sensed by the sensor 217.

The drain pump 225 may pump the water stored in the water collecting space 212 on a regular basis and move the water to the drain container 130. The drain pump 225 may move the water stored in the water collecting space 212 to the drain container 130 on a regular basis regardless of the signal of the sensor 217. Therefore, even if the sensor 217 is broken, water stored in the water collecting space 212 inside the duct 211 may be prevented from overflowing.

Figure 9:
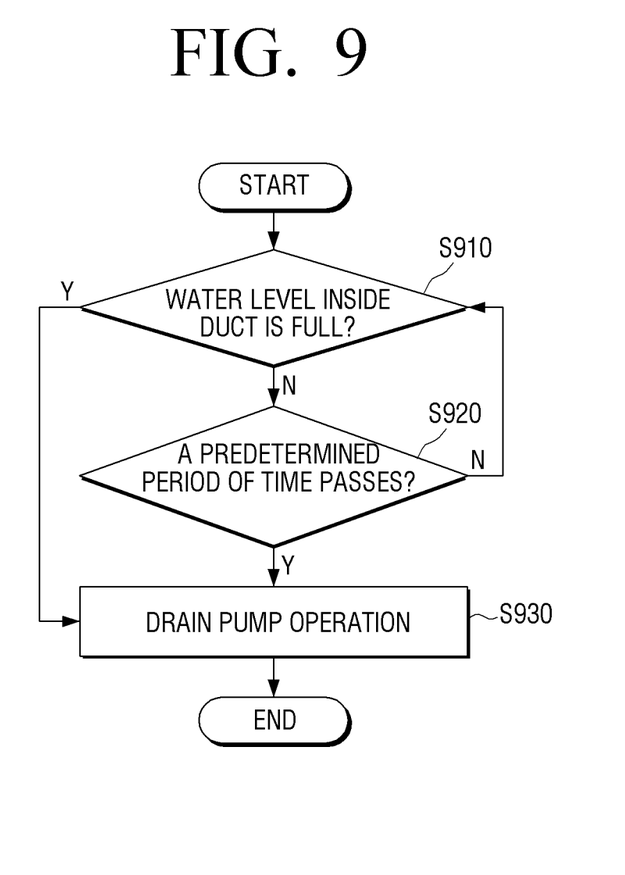
FIG. 9 is a flowchart of a controlling method of a clothing treatment apparatus according to an embodiment of the disclosure.

FIG. 9 is a flowchart of a controlling method of a clothing treatment apparatus according to an embodiment of the disclosure.

Referring to FIG. 9, when the operation of the clothing treatment apparatus 1 is performed by a user, whether the water collecting space 212 of the duct 211 is a full water level may be identified in step 910. When the water collecting space 212 is a full water level, the drain pump 255 may operate in step S930.

When the drain pump 225 is operated, the water stored in the water collecting space 212 may move along the drainage 220 to be stored in the drain container 130. The water stored in the drain container 130 may be removed by the user.

When a predetermined period of time passes after the drain pump 225 is driven, whether the change of the level of water of the water collecting space 212 occurs, and if the change of the water level of the water collecting space 212 occurs, the driving of the drain pump 225 may be stopped. The drain pump 225 may maintain a stop state until the sensor 217 detects that the water collecting space 212 is a full water level.

Whether a predetermined period of time passes may be determined in step S920. When the predetermined period of time passes, the drain pump 225 may operate in step S930.

The drain pump 225 may transfer water in the water collecting space 212 to the drain container 130 at a predetermined time on a regular basis even if the water level is not full.

Even if the sensor 217 itself has an error, it is possible to prevent the water of the duct 211 from overflowing by discharging the water in the duct 211 to the drain container 130 at a predetermined period of time.

In the above, the disclosure has been described by way of example. The terminology used herein is for the purpose of description and should not be regarded as limiting. Many modifications and variations of the disclosure are possible in light of the above teachings. Accordingly, unless otherwise indicated, the disclosure may be embodied freely within the scope of the claims.

What is claimed is:

1. A clothing treatment apparatus, comprising:
a body including a storage chamber that stores clothing;
a spray member configured to spray steam toward the clothing;
a steam generator configured to supply steam to the spray member;
a cabinet provided under the storage chamber; and
a water supply container configured to store water inside, the water supply container being detachably combined with the cabinet,
wherein the cabinet includes a cabinet plate formed with a supply hole that connects the water supply container to the steam generator and a discharge hole that drains residual water discharged when the water supply container is detached.

2. The apparatus as claimed in claim 1, wherein the cabinet plate includes an inclined surface that is formed to be inclined downwardly toward the discharge hole.

3. The apparatus as claimed in claim 1, further comprising:
a duct formed with a water collecting space for collecting condensed water generated from inside the clothing treatment apparatus,
wherein the discharge hole is connected to the duct.

4. The apparatus as claimed in claim 3, further comprising:
a discharge route including one side connected to the discharge hole, and the other end connected to an inlet hole formed in the duct.

5. The apparatus as claimed in claim 4, wherein the discharge hole is formed above the inlet hole formed in the duct.

6. The apparatus as claimed in claim 3, wherein the duct includes a sensor provided in the water collecting space for detecting a level of water in the water collecting space.

7. The apparatus as claimed in claim 6, further comprising:
a drain pump configured to pump condensed water collected in the water collecting space; and
a drain container configured to store water supplied by the drain pump.

8. The apparatus as claimed in claim 7, further comprising:
a processor configured to confirm an amount of water in the water collecting space based on the level of water detected by the sensor, and based on the amount of water in the water collecting space being equal to and more than a predetermined amount, control the drain pump to supply the water in the water collecting space to the drain container.

9. The apparatus as claimed in claim 8, wherein the processor is further configured to control the drain pump to supply the water in the water collecting space to the drain container at a predetermined period of time.

* * * * *

UNITED STATES PATENT AND TRADEMARK OFFICE
CERTIFICATE OF CORRECTION

| | | |
|---|---|---|
| PATENT NO. | : 11,441,258 B2 | Page 1 of 1 |
| APPLICATION NO. | : 16/563115 | |
| DATED | : September 13, 2022 | |
| INVENTOR(S) | : Dongpil Seo et al. | |

It is certified that error appears in the above-identified patent and that said Letters Patent is hereby corrected as shown below:

On the Title Page

Column 1, Line 5, Item (72), insert --Sangho SHIN, Suwon-si, KR--

Signed and Sealed this
First Day of October, 2024

Katherine Kelly Vidal
*Director of the United States Patent and Trademark Office*